(12) United States Patent
Rekimoto (10) Patent No.: US 8,641,634 B2
(45) Date of Patent: Feb. 4, 2014

(54) INFORMATION PROCESSING APPARATUS, INFORMATION PROCESSING METHOD AND PROGRAM

(75) Inventor: Junichi Rekimoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 1100 days.

(21) Appl. No.: 12/272,052

(22) Filed: Nov. 17, 2008

(65) Prior Publication Data

US 2009/0143688 A1  Jun. 4, 2009

(30) Foreign Application Priority Data

Dec. 3, 2007 (JP) ................................ 2007-312665

(51) Int. Cl.
*A61B 5/02* (2006.01)
*A61B 5/05* (2006.01)

(52) U.S. Cl.
USPC .......................................... 600/504; 600/425

(58) Field of Classification Search
None
See application file for complete search history.

(56) References Cited

U.S. PATENT DOCUMENTS

| 7,616,295 B2 * | 11/2009 | Yokoyama et al. | 356/71 |
| 2006/0268109 A1 | 11/2006 | Miyoshi et al. | |
| 2009/0143688 A1 * | 6/2009 | Rekimoto | 600/504 |

FOREIGN PATENT DOCUMENTS

| JP | 2003-331268 | 11/2003 |
| JP | 2004-272458 | 9/2004 |
| JP | 2005-165670 | 6/2005 |
| JP | 2006-285487 | * 10/2006 |
| JP | 2007-128304 | 5/2007 |

OTHER PUBLICATIONS

Text image of JP 2006-285487 on Oct. 19, 2006; inventor: Ota.*

* cited by examiner

*Primary Examiner* — Shanon A Foley
(74) *Attorney, Agent, or Firm* — Finnegan, Henderson, Farabow, Garrett & Dunner, L.L.P.

(57) ABSTRACT

An information processing apparatus according to the present invention includes an imaging section which emits light to a part of a biologic body at predetermined time intervals and images a vein in the biologic body so as to generate imaged data about the vein, a vein pattern extracting section which extracts vein patterns from the imaged data about the vein, a time change detecting section which detects a time change in the vein patterns, a blood flow volume calculating section which calculates a blood flow volume in the vein based on the time change in the vein patterns, and a processing section which executes a predetermined process based on the time change in the vein patterns and a time change in the blood flow volume.

8 Claims, 7 Drawing Sheets

INFORMATION PROCESSING APPARATUS, INFORMATION PROCESSING METHOD AND PROGRAM

CROSS-REFERENCE TO RELATED APPLICATION

The present invention contains subject matter related to Japanese Patent Application JP 2007-312665 filed in the Japan Patent Office on Dec. 3, 2007, the entire contents of which being incorporated herein by reference.

BACKGROUND OF THE INVENTION

1. Field of the Invention

The present invention relates to an information processing apparatus, an information processing method and a program.

2. Description of the Related Art

A method for authenticating a person based on physical features includes an authenticating method for registering person's fingerprint, voice pattern, iris, retina, and vein patterns of back of person's hand and finger as registration data in advance, and comparing data input at the time of authentication with the registration data so as to make a determination. An attention has been paid particularly to person authentication based on vein patterns because of high discrimination property.

In recent years, such vein patterns have been tried to be used for not only person authentication but also an operating unit of an information processing apparatus (for example, see Japanese Patent Application Laid-Open Nos. 2005-165670 and 2007-128304).

SUMMARY OF THE INVENTION

When biological information such as a blood flow volume can be also detected besides the physical features such as vein patterns, advanced input interfaces can be realized. The above patent document, however, does not disclose details of a method for detecting a vein pattern as a physical feature and a blood flow volume as personal biological information using one detecting unit. For this reason, the detecting method which can realize such detection is desired.

It is, therefore, desirable to provide an information processing apparatus and an information processing method and a program which are capable of detecting a vein pattern as a physical feature and a blood flow volume as personal biological information using one detecting unit, and are new and improved.

According to an embodiment of the present invention, there is provided an information processing apparatus including: an imaging section which emits light to a part of a biologic body at predetermined time intervals and images a vein in the biologic body so as to generate a plurality of imaged data about the vein; a vein pattern extracting section which extracts vein patterns from the plurality of imaged data about the vein; a time change detecting section which detects a time change in the vein patterns based on the plurality of vein patterns; a blood flow volume calculating section which calculates a blood flow volume in the vein based on the time change in the vein patterns; and a processing section which executes a predetermined process based on the time change in the vein patterns and a time change in the blood flow volume.

According to such a constitution, the imaging section emits light to a part of a biological body at predetermined time intervals and images a vein in the biological body so as to generate a plurality of imaged data about the vein. The vein pattern extracting section extracts vein patterns from the plurality of imaged data about the vein. The time change detecting section detects a time change in the vein patterns based on the plurality of vein patterns. The blood flow volume calculating section calculates a blood flow volume in the vein based on the time change in the vein patterns. The processing section executes a predetermined process based on the time change in the vein patterns and a time change in the blood flow volume. In the information processing apparatus 10 according to the present invention, not only a vein pattern but also a time change in the vein pattern and a blood flow volume in a vein can be calculated only by imaging a body surface. For this reason, the extracted vein pattern can be used effectively as an input interface.

The blood flow volume calculating section may calculate the blood flow volume based on a thickness change in the vein patterns.

The processing section may control execution of applications to be executed by the information processing apparatus based on the blood flow volume.

The information processing apparatus further includes an input section which inputs a predetermined instruction for the information processing apparatus, and the imaging section may be formed integrally with the input section.

The time change detecting section may track a time change in feature points in the vein patterns so as to detect the time change in the vein patterns.

The processing section may control a movement of a position specifying object of the information processing apparatus according to a position change and rotation of the vein patterns.

The processing section may control an input of the information processing apparatus according to a change in shapes of the vein patterns.

The information processing apparatus further includes an authenticating section which authenticates the vein patterns, and in the information processing apparatus, one vein pattern is related to one application and is stored, and the processing section may actuate the application related to the authenticated vein pattern according to the authenticated vein pattern.

According to another embodiment of the present invention, there is provided an information processing method including the steps of: emitting light to a part of a biologic body at predetermined time intervals and imaging a vein in the biologic body so as to generate imaged data about the vein; extracting vein patterns from the imaged data about the vein; detecting a time change in the vein patterns; calculating a blood flow volume in the vein based on the time change in the vein patterns; and executing a predetermined process based on the time change in the vein patterns and a time change in the blood flow volume.

According to still another embodiment of the present invention, there is provided a program which allows a computer to realize: an imaging function which emits light to a part of a biologic body at predetermined time intervals and images a vein in the biologic body so as to generate a plurality of imaged data about the vein; a vein pattern extracting function which extracts vein patterns from the plurality of imaged data about the vein; a time change detecting function which detects a time change in the vein patterns based on the plurality of vein patterns; a blood flow volume calculating function which calculates a blood flow volume in the vein based on the time change in the vein patterns; and a processing function which executes a predetermined process based on the time change in the vein patterns and a time change in the blood flow volume.

According to such a constitution, computer programs are stored in the storage section provided to the computer, and are read by CPU provided to the computer so as to be executed. As a result, the computer is allowed to function as the information processing apparatus. A recording medium, in which the computer programs are recorded and which can be read by the computer, can be also provided. Examples of the recording medium include a magnetic disc, an optical disc, a magneto-optical disc, and a flash memory. Further, the computer programs may be delivered via network without using the recording medium.

According to the embodiments of the present invention described above, since a vein pattern which is a physical feature and a blood flow volume as personal biological information can be detected by one detecting unit, a vein pattern can be used effectively as an interface of the information processing apparatus.

DETAILED DESCRIPTION OF THE PREFERRED EMBODIMENTS

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

First Embodiment

<Constitution of Information Processing Apparatus>

Figure 1:
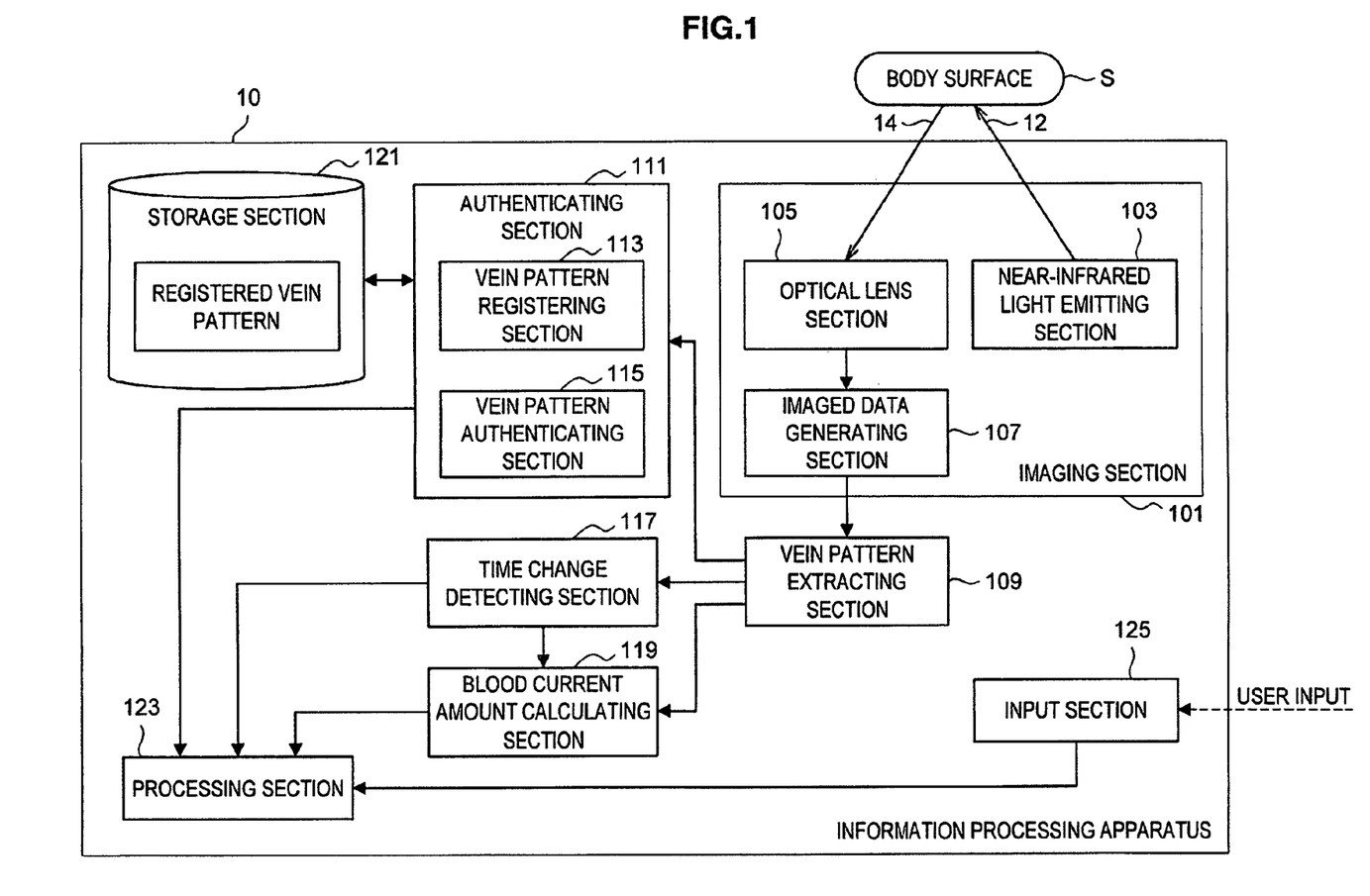
FIG. 1 is a block diagram illustrating a constitution of an information processing apparatus according to a first embodiment of the present invention.

A constitution of an information processing apparatus 10 according to a first embodiment of the present invention is described in detail below with reference to FIG. 1. FIG. 1 is an explanatory diagram describing the constitution of the information processing apparatus 10 according to the first embodiment.

The information processing apparatus 10 according to the first embodiment mainly includes an imaging section 101, a vein pattern extracting section 109, an authenticating section 111, a time change detecting section 117, a blood flow volume calculating section 119, a storage section 121, a processing section 123, and an input section as shown in FIG. 1.

The imaging section 101 images a personal body surface S whose vein pattern is desired to be registered or authenticated at predetermined time intervals so as to generate imaged data. That is to say, every time when predetermined time elapses, the imaging section photographs the body surface S. The time interval at which the body surface S is imaged can be set to any value according to a processing ability of the information processing apparatus 10 according to the first embodiment, but it is set to about 30 frames/sec. The imaging section 101 further includes a near-infrared light emitting section 103, an optical lens section 105, and an imaged data generating section 107, for example. The near-infrared light emitting section 103 emits near-infrared light with predetermined wavelength. The optical lens section 105 condenses light which enters the inside of a body through the body surface S and emits from the inside of the body. The imaged data generating section 107 generates imaged data based on the condensed light.

The near-infrared light emitting section 103 is a light source which emits light with predetermined wavelength to the body surface S. The near-infrared light emitting section 103 is a halogen lamp, light-emitting diodes and the like, and emits near-infrared light 12 having a wavelength of about 600 nm to 1300 nm.

The near-infrared light has high permeableness with respect to body tissue, whereas has a feature such that this light is absorbed by hemoglobin in blood (reduced hemoglobin). For this reason, when the near-infrared light is emitted to a finger, a palm or the back of hand, veins which distribute inside the finger, the palm and the back of hand appear as shadows on an image. The shadow of the vein which appears on the image is called as a vein pattern.

The optical lens section 105 condenses near-infrared light 14 which enters the inside of the body from the body surface S such as a finger surface and is emitted from the inside of the body, and images the light in the imaged data generating section 107. The optical lens section 105 is provided with an optical lens which condenses the near-infrared light 14. The optical lens may include one lens or may include a plurality of lenses. As the optical lens, any lens can be used as long as it can condense near-infrared light efficiently.

The imaged data generating section 107 generates imaged data based on the near-infrared light 14 imaged by the optical lens section 105. The imaged data generating section 107 is, for example, CCD (Charged-Coupled Device) type image sensor or a C-MOS (complementary-Metal Oxide Semiconductor) image sensor. The imaged data generating section 107 outputs the imaged data to the vein pattern extracting section

109, mentioned later. The imaged data generating section 107 may store the generated imaged data in the storage section 121, mentioned later. At the time of the storage in the storage section 121, the generated imaged data may be related to a photographing date, a photographing time and the like. The imaged data to be generated may be a RGB (Red-Green-Blue) signal or image data of the other colors or grey scale.

The vein pattern extracting section 109 may be a CPU (Central Processing Unit), a ROM (Red Only Memory), a RAM (Random Access Memory) or the like. The vein pattern extraction section 109 has a function for executing a pre-process of vein pattern extraction on a plurality of near-infrared light imaged data transmitted from the imaged data generating section 107 at a predetermined time interval, a function for extracting a vein pattern, and a function for executing a post-process of the vein pattern extraction.

The pre-process of the vein pattern extraction includes a process for detecting an outline of a finger from near-infrared light imaged data so as to discriminate a position in the near-infrared light imaged data where the finger is present, and a process for rotating the near-infrared light imaged data using the detected outline of the finger so as to correct an angle of the near-infrared light imaged data (angle of a picked-up image).

The vein pattern extraction is carried out by using a difference filter for the near-infrared light imaged data whose outline has been detected and whose angle has been corrected. The difference filter is a filter which outputs a large value as an output value on a portion where a difference between a target pixel and peripheral pixels is large. In other words, the difference filter is a filter which enhances a line and an edge of an image by means of a calculation using a difference between a target pixel and a vicinity gradation value.

Inn general, when a filter process is executed on image data u (x,y) where a grid point (x,y) on a two-dimensional plane is a variable number using a filter h (x,y), as expressed by the following formula 1, image data v (x,y) is generated. "*" in the following formula 1 represents convolution integral.

$$v(x, y) = u(x, y) * h(x, y) \quad \text{(Formula 1)}$$
$$= \sum_{m_1} \sum_{m_2} h(m_1, m_2) u(x - m_1, y - m_2)$$
$$= \sum_{m_1} \sum_{m_2} u(m_1, m_2) h(x - m_1, y - m_2)$$

In the vein pattern extraction according to the first embodiment, a differentiation filter such as a primary space differentiation filter or a secondary space differentiation filter may be used as the difference filter. The primary space differentiation filter is a filter which calculates a difference in a gradation value between a target pixel and adjacent pixels in lateral and longitudinal directions. The secondary space differentiation filter is a filter which extracts a portion of a target pixel where a change amount of the difference in the gradation value is large.

As the secondary space differentiation filter, for example, a Log (Laplacian of Gaussian) filter described below can be used. The Log filter (formula 3) is expressed by secondary differentiation of a Gaussian filter (formula 2) as a smoothing filter using a Gauss function. In the following formula 2, σ represents a standard deviation of the Gauss function, and is a variable which represents a degree of smoothing of the Gaussian filter. "σ" in the following formula 3 is a parameter representing a standard deviation of the Gauss function similarly to the formula 2, and when the value σ is changed, an output value in the case where the Log filter process is executed can be changed.

$$h_{gauss}(x, y) = \frac{1}{2\pi\sigma^2} \exp\left\{-\frac{(x^2 + y^2)}{2\sigma^2}\right\} \quad \text{(Formula 2)}$$

$$h_{Log}(x, y) = \nabla^2 \cdot h_{gauss}(x, y) \quad \text{(Formula 3)}$$
$$= \left(\frac{\partial^2}{\partial x^2} + \frac{\partial^2}{\partial y^2}\right) h_{gauss}$$
$$= \frac{(x^2 + y^2 - 2\sigma^2)}{2\pi\sigma^6} \exp\left\{-\frac{(x^2 + y^2)}{2\sigma^2}\right\}$$

The post process of the vein pattern extraction includes a threshold process, a binarizing process and a thinning process which are executed on image data to which the difference filter is applied. After such a post process, a skeleton of a vein pattern can be extracted.

The vein pattern extracting section 107 transmits the vein pattern and the skeleton extracted in such a manner to the authenticating section 111, the time change detecting section 117 and the blood flow volume calculating section 119, described later. The vein pattern extracting section 107 may store the extracted vein pattern and skeleton in the storage section 121, described later. The vein pattern extracting section 107 may store parameters generated at the time of the respective processes and the processes in progress in the storage section 121.

The authenticating section 111 may be, for example, CPU, ROM or RAM, and it registers a vein pattern generated by the vein pattern extracting section 109 as a template, compares the vein pattern generated by the vein pattern extracting section 109 with the registered templates so as to authenticate the vein pattern. The authenticating section 111 further includes a vein pattern registering section 113 and a vein pattern authenticating section 115.

The vein pattern registering section 113 registers the vein pattern generated by the vein pattern extracting section 109 as a template. At the time of registering the registration vein pattern, not only the vein pattern but also another data which specifies a person having the vein pattern (for example, fingerprint data, face image data, iris data and voice pattern data) which are related to the vein pattern may be stored. Further, the registration vein pattern to be registered as the template may have header information based on a standard of CBEFF (Common Biometric Exchange File Format).

The vein pattern authenticating section 115 authenticates a generated vein pattern based on the vein pattern generated by the vein pattern extracting section 109 and the template of the registered vein patterns. The vein pattern authenticating section 115 requests the storage section 121, descried later, to disclose the registration vein pattern, and compares the acquired registration vein pattern with the vein pattern transmitted from the vein pattern extracting section 109. The comparison of the registration vein pattern with the transmitted vein pattern can be made based on a correlation coefficient, described below, which is calculated. When the registration vein pattern is similar to the transmitted vein pattern as a result of the comparison, the vein pattern authenticating section 115 authenticates the transmitted vein pattern, and when not similar, it does not authenticate.

The correlation coefficient is defined by the following formula 4, and is a statistics index representing similarity between two data x={$x_i$}, y={$y_i$}, and obtains a real value from −1 to 1. When the correlation coefficient obtains a value close to 1, the two data are similar to each other, and when the correlation coefficient obtains a value close to 0, the two data are not similar. When the correlation coefficient obtains a value close to −1, codes of the two data are inverted.

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \quad \text{(Formula 4)}$$

$\bar{x}$: an average value of data x
$\bar{y}$: an average value of data y

The vein pattern authenticating section 115 correlates the authenticated result to authentication time or the like and may record it as authentication history in the storage section 121. When such an authentication history is generated, a person who authenticates the vein pattern and time when the vein pattern is authenticated can be acquired. After all, a person who uses the information processing apparatus 10 and time when the information processing apparatus 10 is used can be acquired.

The time change detecting section 117 is, for example, CPU, ROM or RAM, and it detects a time change of an image showing a vein pattern based on a plurality of vein patterns transmitted from the vein pattern extracting section 109. Since the vein pattern extracting section 109 extracts a plurality of continuous vein patterns based on imaged data photographed at a predetermined time interval, these vein patterns are used so that a change according to a time course of the image showing a vein pattern can be detected. Concretely, the time change detecting section 117 extracts a feature point such as a folding point from a vein pattern at a certain time, and detects a time change of the extracted feature point using a feature point tracking algorithm such as a KLT (Kanade-Lucas-Tomasi) method. In general, since the time change of the vein pattern is mainly a change due to enlargement, reduction and rotation of an image (so-called affine transformation), the time change can be tracked by using the algorithm such as the KLT method.

When a user of the information processing apparatus 10 intentionally applies a power to a body surface such as a finger surface, it is considered that a vein pattern is deformed according to a pressure. The time change detecting section 117, therefore, pays an attention to a distance between two feature points in a vein pattern at certain time point and tracks the time change of the distance between the two points so as to be capable of detecting a change in the pressure to be applied to the body surface (namely, the change is such that the pressure is applied or the pressure is removed).

The time change detecting section 117 outputs the time change of the vein pattern to the blood flow volume calculating section 119 and the processing section 123, described later. The time change detecting section 117 may record the detected time change of the vein pattern in the storage section 121.

The blood flow volume calculating section 119 is, for example, CPU, ROM or RAM, and it calculates a blood flow volume of blood flowing in a vein based on the time change in the vein pattern detected by the time change detecting section 117. Concretely, the blood flow volume calculating section 119 pays an attention to a time change in thickness of the vein pattern so as to calculate the blood flow volume. Since the blood flow volume changes depending on a degree of user's tension and a pressure to be applied to a body surface, an attention is paid to such a volume so that parameters other than the blood flow volume can be understood.

In related art, the measurement of the blood flow volume is taken by performing a predetermined operation on an entire object to be measured such as a finger and determining the blood flow volume of the object to be measured. The blood flow volume calculating section 119 according to the first embodiment, however, pays an attention not to the entire object to be measured but to a change in a limited portion such as a vein pattern. For this reason, the blood flow volume can be calculated more precisely.

The storage section 121 stores a registration vein pattern which is requested to be registered by the vein pattern registering section 113 and another data related to the registration vein pattern therein. Besides these data, the storage section 121 can store imaged data generated by the imaged data generating section 107 and a vin pattern extracted by the vein pattern extracting section 109 therein. Further, besides these data, the information processing apparatus 10 can appropriately store various parameters necessary for saving at the time of a certain process, a process in progress, and various databases therein. The imaging section 101, the vein pattern extracting section 109, the authenticating section 111, the time change detecting section 117, and the blood flow volume calculating section 119 can freely carry out writing into storage section 121.

The processing section 123 is, for example, CPU, ROM or RAM, and it executes a predetermined process based on at least any one of the time change of a vein pattern transmitted from the time change detecting section 117 and the blood flow volume in a vein transmitted from the blood flow volume calculating section 119. Further, the processing section 123 may execute a predetermined process based on an authenticated result of a vein pattern transmitted from the authenticating section 111 and a predetermined input signal transmitted from the input section 125, described later, in addition to the time change and the blood flow volume. The processing section 123 is described in detail below.

The input section 125 is, for example, CPU, ROM, RAM or an input device, and it inputs an operation for performing a predetermined operation into the information processing apparatus 10. The input section 125 converts the operation input by a user into a predetermined input signal so as to post it to the processing section 123. Examples of the input device include a touch panel, cursor keys, various buttons and a keyboard for controlling a position specifying object such as a cursor pointer.

The input section 125 may be formed integrally with the imaging section 101. When the imaging section 101 is integral with the input section 125, the user of the information processing apparatus 10 can input a predetermined operation into the information processing apparatus 10 and also can photograph a body surface. As a result, the operability of the information processing apparatus 10 can be improved.

<Concrete Example of the Processing Section 134>

Examples of the process to be executed by the processing section 123 according to the first embodiment are described in detail below with reference to FIGS. 2A to 5. FIGS. 2A to 5 are explanatory diagrams describing examples of the process to be executed by the processing section according to the first embodiment.

<Process According to Movement and Rotation of Vein Pattern>

Figure 2A:
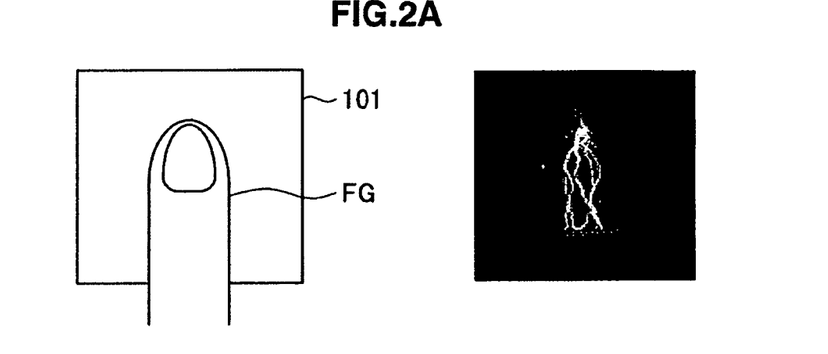
FIG. 2A is an explanatory diagram describing one example of a process to be executed by a processing section according to the first embodiment.
Figure 2B:
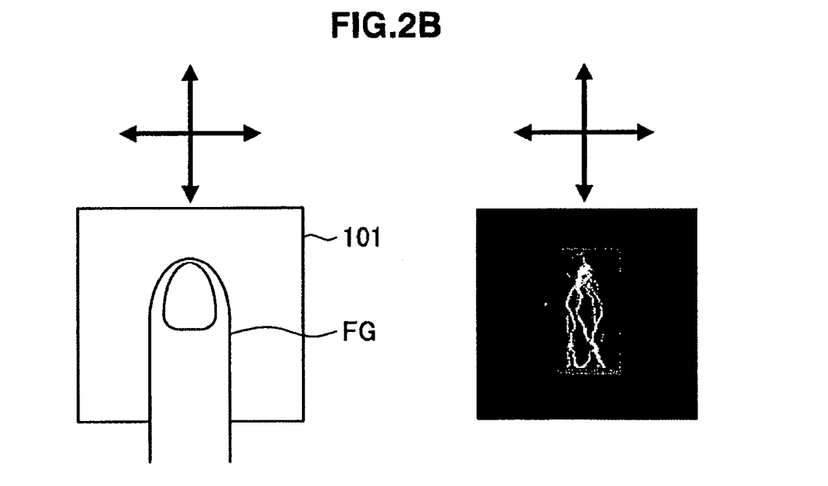
FIG. 2B is an explanatory diagram describing one example of the process to be executed by the processing section according to the first embodiment.
Figure 2C:
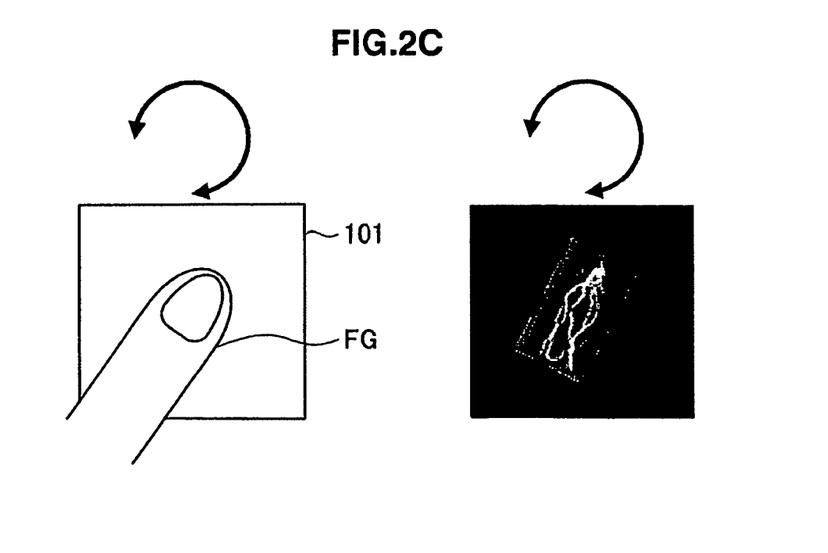
FIG. 2C is an explanatory diagram describing one example of the process to be executed by the processing section according to the first embodiment.

As shown in FIGS. 2A to 2C, a vein pattern can be used for operating the position specifying object such as a mouse pointer.

As shown in FIG. 2A, when a finger FG is brought into contact with the imaging section 101, a vein pattern in a right part of the drawing can be obtained. As shown in FIG. 2B, when the finer FG is moved up, down, right and left, the vein pattern also moves up, down, right and left according to the movements of the finger FG. As shown in FIG. 2C, when the finger FG rotates about a contact surface with the imaging section 101, the vein pattern also rotates about a certain point.

When the finger FG is placed on an imaging surface of the imaging section 101, the imaging section 101 according to the first embodiment continuously images the finger FG at an interval of about 30 frames/sec so as to generate a plurality of imaged data. The vein pattern extracting section 109 extracts vein patterns from the obtained image data. The time change detecting section 117 checks the time change in the plurality of vein patterns so as to be capable of specifying movements of the finger. That is to say, the time change detecting section 117 detects the time change in the vein pattern, so as to be capable of detecting movements/non-movements and rotation/non-rotation of the vein pattern, moving directions of the vein pattern, and a rotating direction of the vein pattern. The processing section 123 controls a movement and a rotation of the position specifying object such as a mouse pointer or a cursor according to the moving direction and the rotating direction of the vein pattern detected by the time change detecting section 117.

When the time change detecting section 117 detects the time change in the vein pattern, the blood flow volume calculating section 119 calculates the blood flow volume in the vein of the finger FG. The blood flow volume calculating section 119 may calculate the time change in the calculated blood flow volume. When the blood flow volume is calculated, a state of a user as an operator such that the user feels pressed or is tense can be understood. For this reason, the processing section 123 may quicken or slow down a moving speed of the position specifying object according to the detected user's state.

(Process According to Modification of Vein Pattern)

A case where a modification according to time course of a vein pattern is used for the operation of the position specifying object such as a mouse pointer is described in detail below with reference to FIGS. 3A to 3E.

Figure 3A:
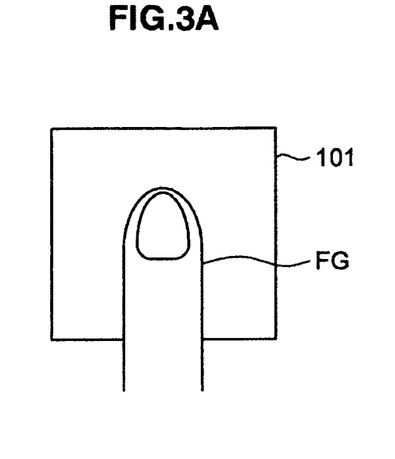
FIG. 3A is an explanatory diagram describing one example of the process to be executed by the processing section according to the first embodiment.
Figure 3B:
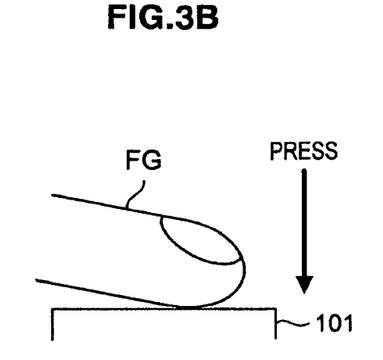
FIG. 3B is an explanatory diagram describing one example of the process to be executed by the processing section according to the first embodiment.
Figure 3C:
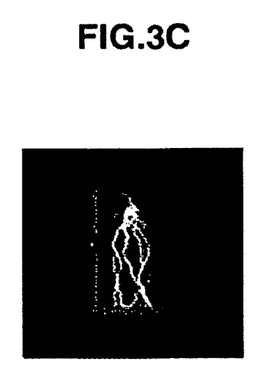
FIG. 3C is an explanatory diagram describing one example of the process to be executed by the processing section according to the first embodiment.
Figure 3D:
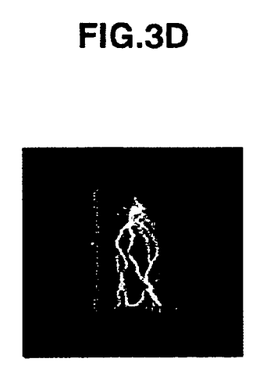
FIG. 3D is an explanatory diagram describing one example of the process to be executed by the processing section according to the first embodiment.
Figure 3E:
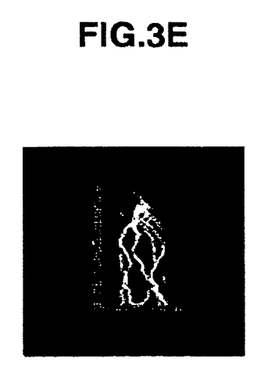
FIG. 3E is an explanatory diagram describing one example of the process to be executed by the processing section according to the first embodiment.

The finger FG is placed on the imaging section 101 as shown in FIG. 3A, and a force is applied to the finger FG in an approximately vertical direction as shown in FIG. 3B. As a result, the contact surface with the imaging section 101 increases, and as shown in FIGS. 3C to 3E, it is considered that a vein pattern to be extracted becomes flat. Therefore, a shape change of the vein pattern is detected so that a change of the finger FG to the vertical direction can be understood.

That is to say, the time change detecting section 117 pays an attention to two feature points in the vein pattern, and tracks a change in a distance between the two points. When the distance between the two points becomes large according to the time change, the time change detecting section 117 determines that the vein pattern becomes flat. The processing section 123 accepts the determined result and determines that an object such an icon is clicked or various buttons are pressed so as to execute predetermined processes related to the operations.

When the vein pattern changes over time from FIG. 3E to FIG. 3C, on the contrary to the above example, the processing section 123 determines that the finger FG moves up in the vertical direction.

The processing section 123 according to the first embodiment tracks the movements of the vein patterns in front, back, right and left directions, the deformation of the vein pattern, and the rotation of the vein pattern. As a result, the time change in the vein pattern can be used for operating the position specifying object.

(Process According to Difference in Authenticated Vein Pattern)

A case where a difference of an authenticated vein pattern is used for actuating an application is described in detail below with reference to FIG. 4.

The user registers vein patterns of thumb $FG_1$ to a little finger $FG_5$ as registration vein patterns in the storage section 121, and relates the vein patterns corresponding to the respective fingers to applications in one-to-one relationship. After the vein patterns are related to the applications, the user allows the information processing apparatus 10 to image the finger FG related to the application desired to be actuated, so as to be capable of actuating the application.

More detailed description is given below. The user places the thumb $FG_1$ on the imaging section 101. As a result, the imaging section 101 generates imaged data about the thumb $FG_1$, and the vein pattern extracting section 109 extracts the vein pattern of the thumb $FG_1$. The vein pattern registering section 113 in the authenticating section 111 records the extracted vein pattern of the thumb $FG_1$ as a registration vein pattern in the storage section 121. The user selects the application to be related to the vein pattern of the vein pattern $FG_1$, so as to relate the application to the vein pattern of the thumb $FG_1$.

Vein patterns of the index finger $FG_2$ to the little finger $FG_5$ are registered similarly and are related to applications.

Figure 4:
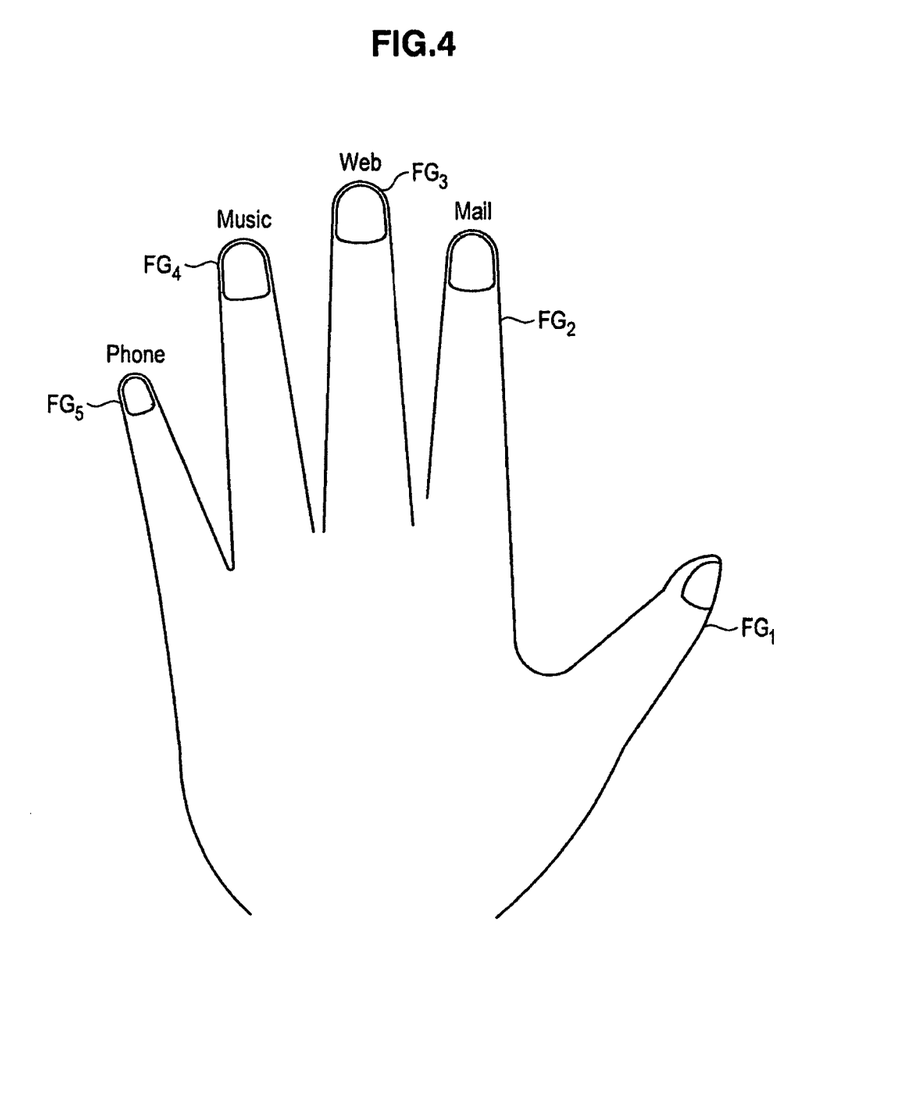
FIG. 4 is an explanatory diagram describing one example of the process to be executed by the processing section according to the first embodiment.

In the example shown in FIG. 4, the index finger $FG_2$ is related to a mail software, and the middle finger $FG_3$ is related to a Web browser. The medicinal finger $FG_4$ is related to a sound source reproducing software, and the little finger $FG_5$ is related to a telephone software. When the mail software is desired to be actuated, for example, the user allows the imaging section 101 to image the index finger $FG_2$ so as to be capable of actuating the mail software.

(Control of Execution of Application According to Blood Flow Volume)

The information processing apparatus 10 according to the first embodiment can calculate the blood flow volume based on the time change of the vein pattern. When the blood flow volume is calculated, the user's state such that the user feels pressed or is tense can be understood. For this reason, execution of an application can be controlled based on the user's state.

When the calculated blood flow volume is not less than a predetermined threshold, the blood flow volume calculating section 119 determines that the user is tense, and controls the execution of application. When the information processing apparatus 10 executes a game as an application, for example, and the user's tense state is transmitted from the blood flow volume calculating section 119, the processing section 123 changes a difficulty level of the on-executing game so as to be capable of heightening or lowering the difficulty level. The processing section 123 may check a user's health state based on the calculated blood flow volume.

Figure 5:
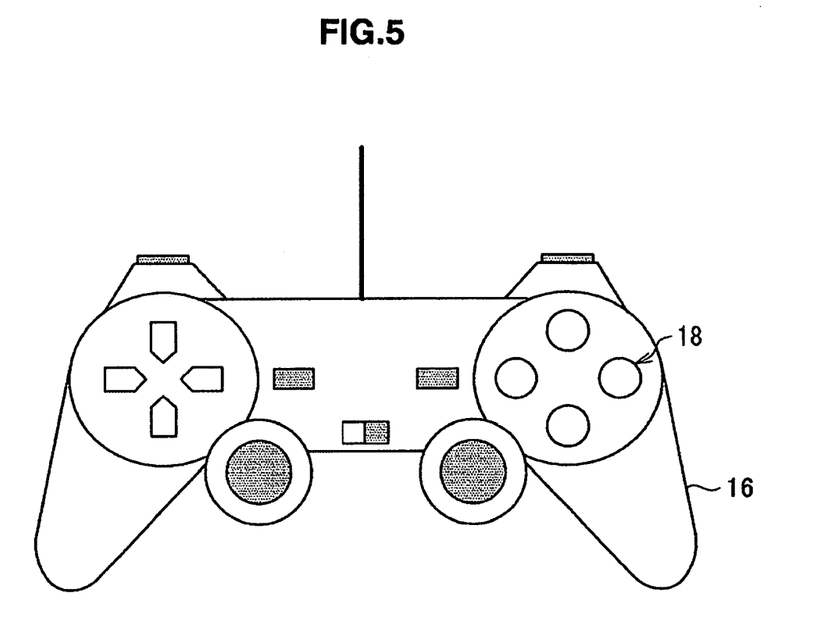
FIG. 5 is an explanatory diagram describing one example of the process to be executed by the processing section according to the first embodiment.

In a game pad 16 shown in FIG. 5, for example, when the imaging section 101 is made to be integral with buttons 18, the user can enjoy a game without regarding to the imaging of a vein pattern (eventually, the calculation of the blood flow volume). When the imaging section 101 is provided below the buttons 18 or the like, a vein pattern can be imaged. For this reason, the vein pattern can be imaged without enlarging the game pad 16.

One example of a function of the information processing apparatus 10 according to the first embodiment is described below. The above-mentioned components may be constituted by using versatile members and circuits, or may be constituted by hardware specialized for the functions of the components. All the functions of the components may be executed by CPU or the like. Therefore, the constitution to be used can be appropriately changed according to each technical level for carrying out the embodiment.

The information processing apparatus 10 according to the first embodiment may be packaged into various apparatuses such as information processing apparatuses including a computer and a server, a mobile terminal and a personal digital assistance (PDA) including a mobile telephone and PHS, an automated teller machine (ATM), an entering/leaving management apparatus, a game machine, and a controller of game machine.

The above description refers to the case where a registration vein pattern to be registered as a template is recorded in the information processing apparatus 10. However, the registration vein pattern may be recorded in recording media such as DVD media, HD-DVD media, Blu-ray media, compact flashes (registered trademark), memory sticks or SD memory cards, IC cards mounted with non-contact type IC chip, or electronic devices. Further, registration vein pattern may be recorded in a server connected to the information processing apparatus 10 via a communication network such as Internet.

<Flow of Information Processing Method>

Figure 6:
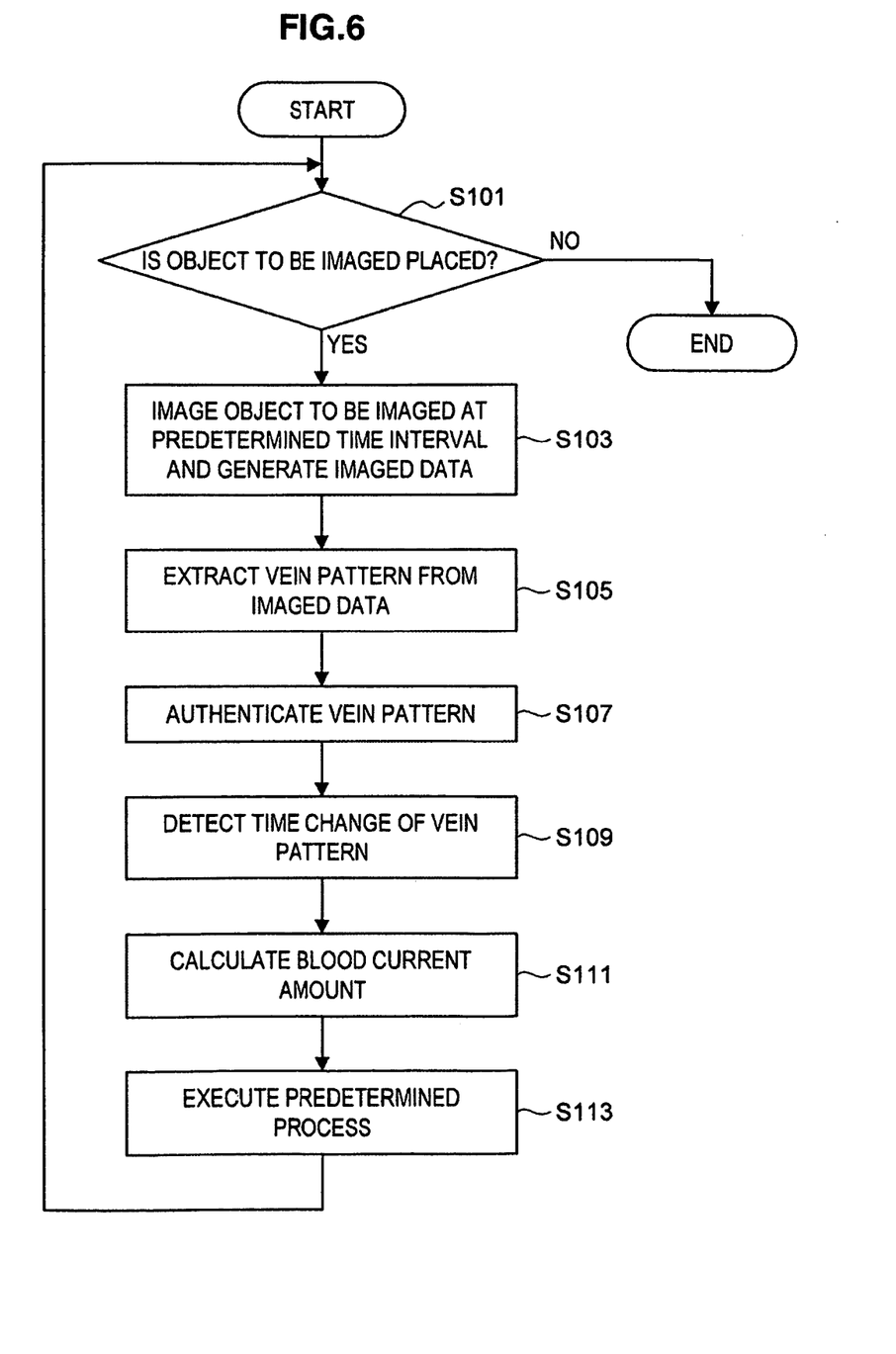
FIG. 6 is a flow chart describing an information processing method according to the first embodiment.

An information processing method in the information processing apparatus according to the first embodiment is described in detail below with reference to FIG. 6. FIG. 6 is a flow chart describing the information processing method according to the first embodiment.

In the information processing method according to the first embodiment, the imaging section 101 determines whether an object to be imaged such as a finger is placed on the imaging surface (step S101). When the object to be imaged is not placed, a process is not executed. When the object to be imaged is placed on the imaging surface, the imaging section 101 images the object to be imaged at predetermined time intervals so as to generate imaged data (step S103).

The vein pattern extracting section 109 extracts vein patterns from the plurality of imaged data based on the above method (step S105) and transmits the plurality of vein patterns to the authenticating section 111, the time change detecting section 117 and the blood flow volume calculating section 119. The vein pattern extracting section 109 may record the extracted vein patterns in the storage section 121.

The authenticating section 111 authenticates the extracted vein patterns (step S107). When the user desires to register the vein patterns, the vein pattern registering section 113 records the extracted vein patterns as registration vein patterns in the storage section 121. When the user does not desire to register the vein patterns, the vein pattern authenticating section 115 compares the registration vein patterns recorded in the storage section 121 with the extracted vein patterns so as to authenticate the extracted vein patterns.

The time change detecting section 117 detects a time change in the vein pattern based on the plurality of vein patterns transmitted from the vein pattern extracting section 109 (step S109) so as to check movements, rotations and deformations of the vein patterns.

The blood flow volume calculating section 119 calculates a blood flow volume in a vein based on the time change in the vein patterns (step s113).

The processing section 123 executes a predetermined process based on at least any one of the detected result in the time change detecting section 117 and the calculated value of the blood flow volume by the blood flow volume calculating section 119 (step S113). The processing section 123 may execute the predetermined process based on the authenticated result of the authenticating section 111 besides the time change in the vein patterns and the blood flow volume.

The above description refers to the case where after the authentication of the vein patterns is completed, the time change in the vein patterns is detected. However, the authentication of the vein patterns and the detection of the time change in the vein patterns may be simultaneously carried out, or after the time change in the vein pattern is detected, the vein patterns may be authenticated.

<Hardware Structure of the Information Processing Apparatus>

Figure 7:
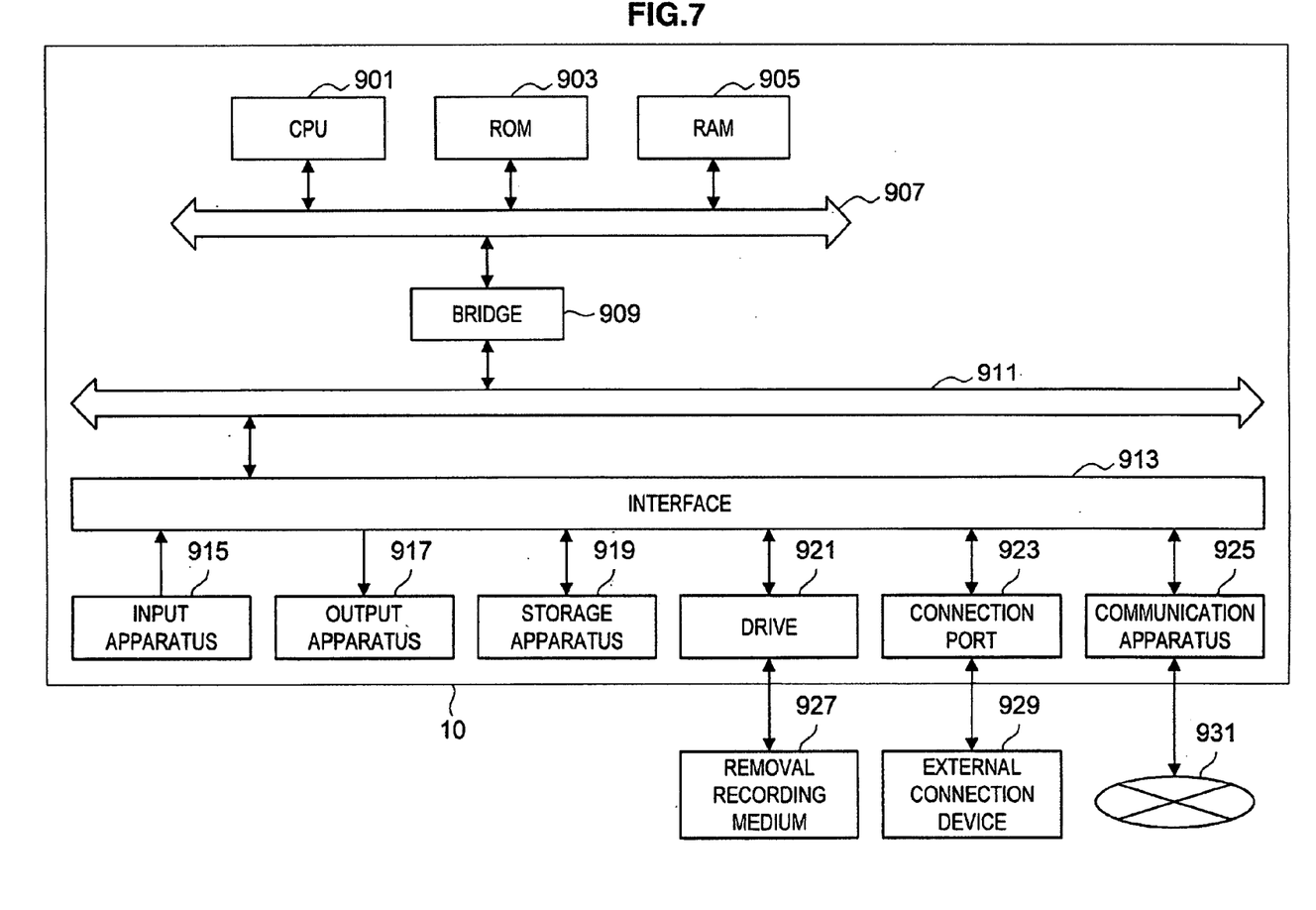
FIG. 7 is a block diagram describing a hardware constitution of the information processing apparatus according to the first embodiment.

The hardware structure of the information processing apparatus 10 according to the first embodiment is described in detail below with reference to FIG. 7. FIG. 7 is a block diagram describing the hardware structure of the information processing apparatus 10 according to the first embodiment.

The information processing apparatus 10 mainly includes a CPU 901, a ROM 903, a RAM 905, a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls an entire or partial operation in the information processing apparatus 10 according to various programs recorded in the ROM 903, the RAM 905, the storage device 919 or a removable recording medium 927. The ROM 903 stores a program or an arithmetic parameter to be used by the CPU 901. The RAM 905 temporarily stores a program to be executed by the CPU 901 and a parameter which appropriately changes due to the execution of the program. They are connected to one another by the host bus 907 made by an internal bus such as a CPU bus.

The host bus 907 is connected to the external bus 911 such as a PCI (Peripheral Component Interconnect/Interface) bus via the bridge 909.

The input device 915 is an operating unit, such as a mouse, a keyboard, a touch panel, a button, a switch or a lever, which is operated by the user. The input device 915 may be, for example, a remote control unit which uses infrared rays and another radio waves, or an external connector 929 such as a mobile telephone or PDA according to the operation of the information processing apparatus 10. The input device 915 is an input control circuit which generates an input signal based on information input by the user using the operating unit and outputs it to the CPU 901. The user of the information processing apparatus 10 operates the input device 915 so as to be capable of inputting various data into the information processing apparatus 10 or instructing a processing operation.

The output device 917 is a device which can post acquired information to the user visually or acoustically. Examples of the device include a display device such as a CRT display device, a liquid crystal display device, a plasma display device, an EL display device and a lamp, an audio output device such as a speaker and a headphone, a printer device, a mobile telephone and a facsimile. The output device 917 outputs results acquired by various processes executed by the information processing apparatus 10. Concretely, the display device displays the results acquired by various processes executed by the information processing apparatus 10 in a text form or an image form. On the other hand, the audio output device converts an audio signal such as reproduced audio data or acoustic data into an analog signal so as to output it.

The storage device 919 is a device for data storage constituted as one example of the storage section of the information processing apparatus 10. The storage device 919 is a magnetic storage device such as HDD (Hard Disk Drive), a semiconductor storage device, an optical storage device or a magneto-optical storage device. The storage device 919 stores programs to be executed by the CPU 901, various data, and acoustic signal data and image signal data acquired from the outside therein.

The drive 921 is a reader/writer for recording media, and is built into or externally mounted to the information processing apparatus 10. The drive 921 reads information recorded in a removal recording medium 927 such as attached magnetic disc, optical disc, magneto-optical disc or semiconductor memory, and outputs it to the RAM 905. The drive 921 can write recording into the removal recording medium 927 such as attached magnetic disc, optical disc, magneto-optical disc or semiconductor memory. The removal recording medium 927 is, for example, DVD media, HD-DVD media, Blu-ray media, compact flashes (registered trademark) (CF), memory sticks or SD memory cards (Secure Digital memory card). Further, the removal recording medium 927 may be an IC card (Integrated Circuit card) mounted with a non-contact IC chip or an electronic device.

The connection port 923 is a port, such as a USB (Universal Serial Bus) port, an IEEE 1394 port such as i. Link, a SCSI (Small Computer System Interface) port, a RS-232C port, an optical audio terminal or an HDMI (High-Definition Multimedia Interface) port, for connecting the devices directly to the information processing apparatus 10. When the external connector 929 is connected to the connection port 923, the information processing apparatus 10 acquires acoustic signal data or image signal data directly from the external connector 929, or provides acoustic signal data or image signal data to the external connector 929.

The communication device 925 is a communication interface constituted by a communication device to be connected to the communication network 931. The communication device 925 is, for example, a communication card for a wired or wireless LAN (Local Area Network), Bluetooth or WUSB (Wireless USB), a router for optical communication, a router for ADSL (symmetric Digital Subscriber Line), or a modem for various communication. The communication device 925 can transmit/receive an acoustic signal to/from Internet or another communication devices. The communication network 931 to be connected to the communication device 925 is a network or the like connected in wired or wireless manner, or may be, for example, internet, domestic LAN, infrared-ray communication, radio wave communication or satellite communication.

The above described one example of the hardware structure which can realize the function of the information processing apparatus 10 according to the embodiment of the present invention. The components may be versatile members, or may be hardware specialized for the functions of the components. Therefore, the hardware structure to be used can be changed appropriately according to every technical level at the time of carrying out the embodiment.

It should be understood by those skilled in the art that various modifications, combinations, sub-combinations and alterations may occur depending on design requirements and other factors insofar as they are within the scope of the appended claims or the equivalents thereof.

For example, the above embodiment describes the case where the reflection type imaging section is provided to the information processing apparatus 10, but a transmission type imaging section may be provided instead of the reflection type imaging section.

What is claimed is:

1. An information processing apparatus comprising:
   an imaging section which emits light to a part of a biologic body at predetermined time intervals and images a vein in the biologic body so as to generate a plurality of imaged data about the vein;
   a vein pattern extracting section which extracts vein patterns from the plurality of imaged data about the vein;
   a time change detecting section which detects a time change in the vein patterns based on the plurality of vein patterns;
   a blood flow volume calculating section which calculates a blood flow volume in the vein based on the time change in the vein patterns; and
   a processing section which determines a change in pressure applied to the biologic body by the imaging section based on the time change in the vein patterns and a time change in the blood flow volume.

2. The information processing apparatus according to claim 1, wherein the blood flow volume calculating section calculates the blood flow volume based on a thickness change in the vein patterns.

3. The information processing apparatus according to claim 2, wherein the processing section controls execution of applications to be executed by the information processing apparatus based on the blood flow volume.

4. The information processing apparatus according to claim 2 further comprising:
   an input section which inputs a predetermined instruction for the information processing apparatus,
   wherein the imaging section is formed integrally with the input section.

5. The information processing apparatus according to claim 1, wherein the time change detecting section tracks a time change in feature points in the vein patterns so as to detect the time change in the vein patterns.

6. The information processing apparatus according to claim 5, wherein the processing section controls a movement of a position specifying object of the information processing apparatus according to a position change and rotation of the vein patterns.

7. The information processing apparatus according to claim 5, wherein the processing section controls an input of the information processing apparatus according to a change in shapes of the vein patterns.

8. The information processing apparatus according to claim 1, further comprising:
   an authenticating section which authenticates the vein patterns,
   wherein one vein pattern is related to one application and is stored,
   the processing section actuates the application related to the authenticated vein pattern according to the authenticated vein pattern.

* * * * *